United States Patent
McPeak et al.

(10) Patent No.: US 6,880,808 B2
(45) Date of Patent: Apr. 19, 2005

(54) GAMMA-STABLE HIGH PRESSURE STOPCOCK

(75) Inventors: Thomas J. McPeak, Shakopee, MN (US); Jon K. Moon, Edina, MN (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 10/138,085

(22) Filed: May 3, 2002

(65) Prior Publication Data

US 2003/0205687 A1 Nov. 6, 2003

(51) Int. Cl.⁷ .................................................. F16K 5/00
(52) U.S. Cl. ...................................... 251/309; 251/312
(58) Field of Search ................................. 251/309–312

(56) References Cited

U.S. PATENT DOCUMENTS

| | | | | |
|---|---|---|---|---|
| 3,788,602 A | * | 1/1974 | Kitzie | 251/312 |
| 3,790,132 A | * | 2/1974 | Schmitt | 251/312 |
| 3,918,680 A | * | 11/1975 | Stevens, Jr. | 251/312 |
| 4,003,403 A | * | 1/1977 | Nehring | 251/309 |
| 4,084,783 A | * | 4/1978 | Wrasman | 249/175 |
| 4,147,184 A | * | 4/1979 | Jess | 251/312 |
| 4,207,923 A | * | 6/1980 | Giurtino | 251/309 |
| 4,314,586 A | * | 2/1982 | Folkman | 251/309 |
| 4,512,364 A | * | 4/1985 | Phillips | 251/309 |
| 4,807,666 A | * | 2/1989 | Morse | 251/309 |
| 5,088,690 A | * | 2/1992 | Stellmacher et al. | 251/309 |
| 6,090,094 A | * | 7/2000 | Clifford, Jr. et al. | 604/500 |
| 6,099,511 A | * | 8/2000 | Devos et al. | 604/246 |

* cited by examiner

*Primary Examiner*—Paul J. Hirsch
(74) *Attorney, Agent, or Firm*—Kramer, Levin, Naftalis & Frankel LLP

(57) ABSTRACT

A medical stopcock is provided that is constructed and arranged to withstand high pressures and gamma irradiation. The stopcock generally includes a housing and a valve member. The valve member is trapped within the housing so that, when subjected to relatively high pressures, the valve member is unlikely to become separated from the housing. A handle member is attached to the valve member and allows the valve member to be rotated from open to closed positions. In some preferred embodiments, the handle member locks the valve member within the housing, when attached. All of the components are constructed of gamma-stable materials so that the stopcock may be sterilized, in its package, using gamma irradiation.

37 Claims, 6 Drawing Sheets

GAMMA-STABLE HIGH PRESSURE STOPCOCK

BACKGROUND OF THE INVENTION

The device of the present invention pertains to a stopcock capable of withstanding gamma radiation. The stopcock is constructed and arranged for high pressure applications.

Gamma radiation is a form of energy capable of deep penetration. Gamma irradiation is the use of gamma radiation to sterilize medical devices. Gamma radiation kills microorganisms throughout a product and its packaging with very little heating. As a sterilant, gamma radiation is thorough; no area of the product, its components, or packaging is left with uncertain sterility after treatment. Furthermore, gamma irradiation leaves no residue.

Traditional sterilization techniques include batch sterilization using ethylene oxide (EtO). EtO sterilization leaves a residue and requires an aeration period prior to shipment. The packaging must be gas permeable to allow the EtO to completely evaporate prior to use. Gas permeable packaging, however, increases the possibility of contamination over time. Thus, a relatively early expiration date is assigned to the sterilized device. Gamma radiation, on the other hand, penetrates through the packaging and, again, leaves no residue.

Commercially-available stopcocks, however, are constructed of materials that are not dimensionally stable when exposed to gamma radiation. Gamma-stable materials are more expensive and more rigid than the softer materials used to form the valve members of the commercially-available stopcocks. FIG. 1 shows a cross-sectional view of a typical, commercially-available stopcock 1. The stopcock 1 includes a valve member 3 inserted into a housing 5. The valve member 3 may be hollow, as shown, or solid and includes a port 7 that can be aligned with passage 9 of the housing 5.

The two-piece construction of the stopcock 1 relies on an interference fit between the valve member 3 and the housing 5. In other words, the valve member 3 is slightly larger than the interior of the housing 5. When the valve member 3 is inserted into the housing 5, it compresses and forms a fluid-tight fit. Thus, the valve member 3 must be constructed of a softer plastic than that of the housing 5. Typical materials used to make these valve members 3 include acetal and acrylonitrile butadiene-styrene (ABS).

Unfortunately, these soft materials used to make the valve members 3 cannot withstand gamma irradiation. When exposed, the valve members 3 change dimension and render the stopcock unusable. Thus, a less effective, more expensive, form of sterilization must be used.

Another disadvantage of these stopcocks 1 pertains to the design of the snap fit between the soft valve member 3 and the housing 5. As seen in FIG. 1, the snap fit arrangement is achieved by providing an angled flange 11 at the lower end of the valve member 3 that is configured to mate with a corresponding inwardly-projecting flange 13 that is integral with the housing 5. To allow assembly and a fluid tight fit, the flanges 11 and 13 have to be relatively small so that the flange 11 on the valve member 3 may deform and reform as it passes over the other flange 13 during assembly. The size relationship between the two flanges 11 and 13 limits the use of these stopcocks 1 for high pressure applications. When subjected to high pressures, there is a tendency for the valve members 3 to be ejected from the housing 5.

A further disadvantage of these stopcocks 1 is that they require excessive turning force to open and close the valves. Because the fluid-tight integrity depends on the friction fit between valve member 3 and the housing 5, and thus the valve member 3 is slightly larger than the housing 5, it is difficult to turn the valve member 3 within the housing 5. Users complain that two hands are necessary to operate the stopcocks 1 without causing the tubing attached to the stopcocks from becoming twisted or dislodged. Further, the relatively small size of the stopcocks 1 make it difficult to grasp the housing 5, to turn the valve member 3, without having fingers interfere with the handle of the valve member 3. This problem is especially prevalent when turning the valve members 3 of high pressure stopcocks while wearing wet rubber gloves.

Additionally, materials like acetal and ABS are opaque, which is yet another disadvantage. For purposes of blood and bubble detection, it is preferable to use a fluid network comprised entirely of clear components.

There is thus a need for a stopcock that can withstand gamma irradiation.

There is a further need for a stopcock that is constructed and arranged to withstand high pressures.

There is also a need for a stopcock that can be opened and closed with relative ease.

There is an additional need for a stopcock that is constructed entirely of clear materials.

BRIEF SUMMARY OF THE INVENTION

The present invention pertains to a stopcock made entirely of materials capable of withstanding sterilization using gamma irradiation. A method of making a stopcock is disclosed that allows a stopcock housing to be formed around the outside of a valve member, thereby providing an improved fit between the valve member and the housing.

The internal valve member is constructed of a rigid material, such as polyetheretherketone (PEEK), capable of withstanding gamma rays without experiencing a change in dimension. The external housing is also constructed of such a material, usually polycarbonate. The housing includes a cylindrical interior cavity with an inner diameter approximately equal to the outer diameter of the valve member. The valve member has a stop, preferably a flange, extending radially from one end to prevent the valve member from passing completely through the housing. The valve member is secured at the other end by attaching a handle member thereto. The attachment is made with an adhesive, snap fit, friction fit, weld (e.g. ultrasonic), pin connection, or the like.

PEEK is just an example of many materials acceptable for use in making the stopcock of the present invention. Other example materials include polyesters, glycol modified polyethylene terepthalate (PETG), polycarbonate, polycarbonate alloys, polysulfone, polyurethane, polyetherketoneketone (PEKK), polyetherimide, thermosets, polyamides, polyaryletherketone (PAEK), and flouroplastics other than polytetrafluoroethylene (PTFE) and fluorinated ethylene propylene (FEP). Examples of acceptable thermosets include polyimides, polyurethanes, and polyesters.

The handle member, valve member and housing all may be made of the same material. However, using materials having slightly different melting points for the housing and the valve member provides an advantageous manufacturing option. If the housing is made of a material with a slightly lower melting point than that of the valve member, the housing may be formed by over molding the valve member. This ensures that the interior cavity of the housing exactly matches the size of the valve member. The difference in melting temperature prevents the housing material from fusing with the valve member.

Alternatively, the process of over-molding may use materials that are not considered gamma-stable as a way of ensuring a close fit between the outer housing and the inner valve member. If the inner valve member and the outer housing are made of materials that react differently when exposed to gamma radiation, the outer housing may be made to shrink around the inner valve member during gamma irradiation. This concept not only creates a water-tight fit between the housing and the valve member, it permits the use of less expensive, non-gamma-stable materials.

Additionally, considering the high cost of gamma-stable materials, it may be desired to provide a non-gamma-stable handle, attachable to a gamma-stable valve member. Doing so would not only provide a cost benefit, especially in the case of large stopcocks, it would also allow design flexibility. For example, it may be desired to provide a variety of handle members having different colors. The colors could then be selected to identify the type of fluid travelling through the stopcock. The valve member may also be designed without a handle, for use with an automatic device constructed and arranged to operate the stopcock.

Further, to provide turning ease, a grip is preferably incorporated into the stopcock housing which can be used to hold the housing while turning the valve member, thereby giving the physician greater turning leverage. The grip may be an axial extension of the housing or may extend radially in a direction where interference with ports is not created.

One aspect of the present invention provides a stopcock having a valve member that is attachable to, or integral with, handle members on either side of the stopcock.

DETAILED DESCRIPTION OF THE INVENTION

Figure 1:
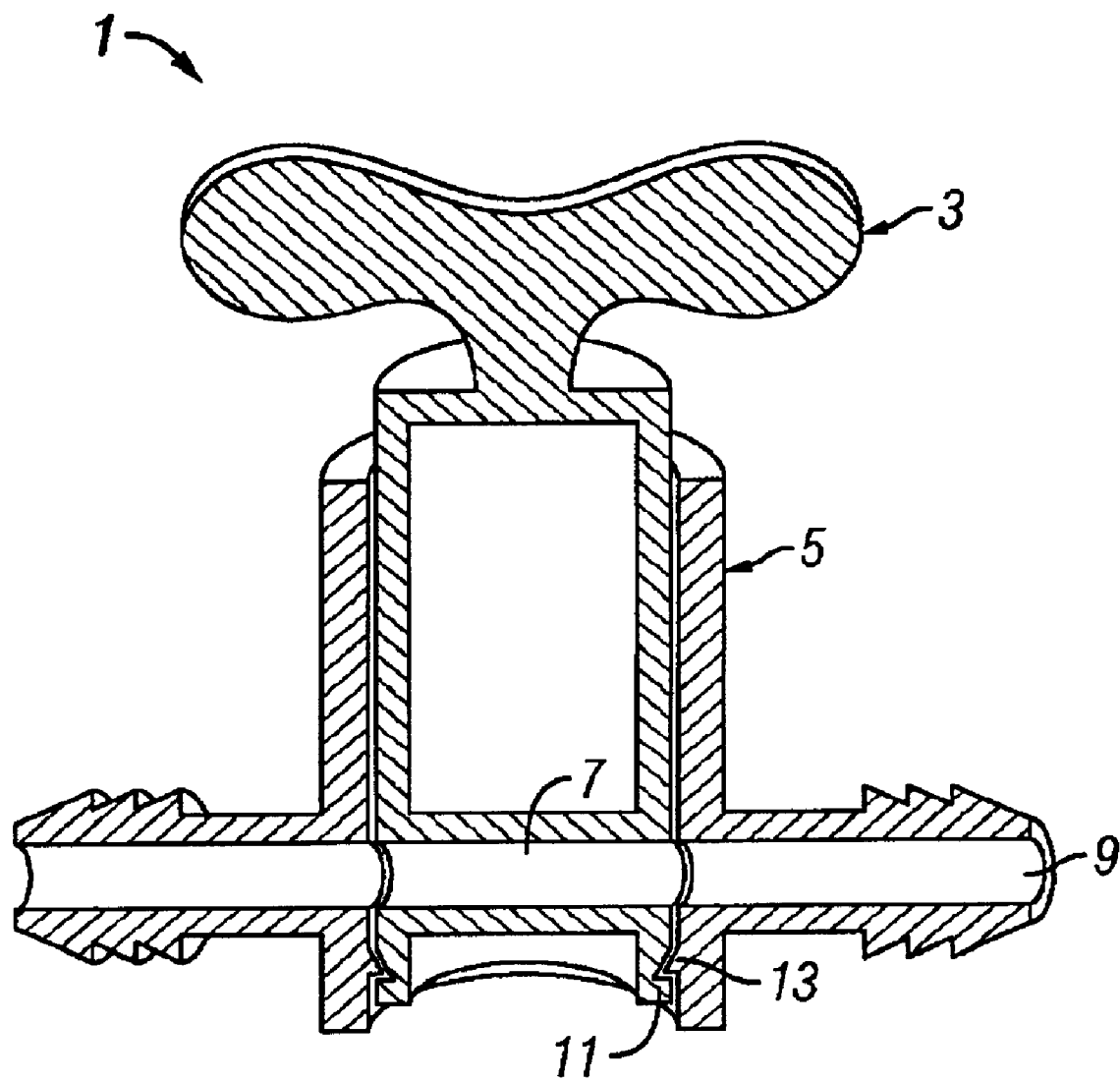
FIG. 1 is a prior art stopcock.
Figure 2:
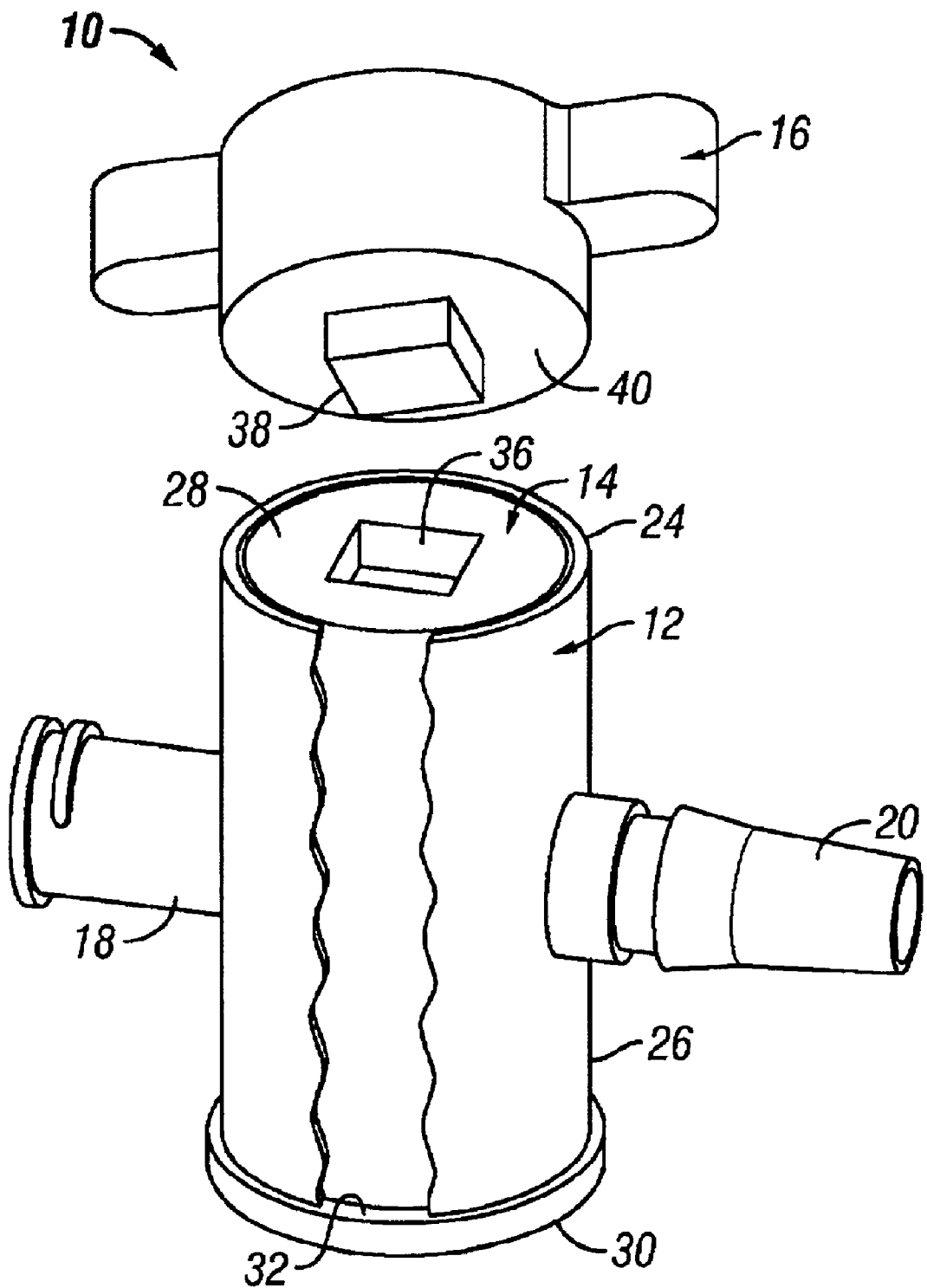
FIG. 2 is a perspective view of a preferred embodiment of the stopcock of the present invention with the handle member separated from the valve member and the housing partially cut away.

Referring now to FIG. 2, there is shown a stopcock 10 of the present invention. The stopcock 10 generally comprises a housing 12, a valve member 14, and a handle member 16. The housing 12, the valve member 14 and the handle member 16 are all preferably made of materials that remain dimensionally stable when exposed to gamma radiation.

Figure 3:
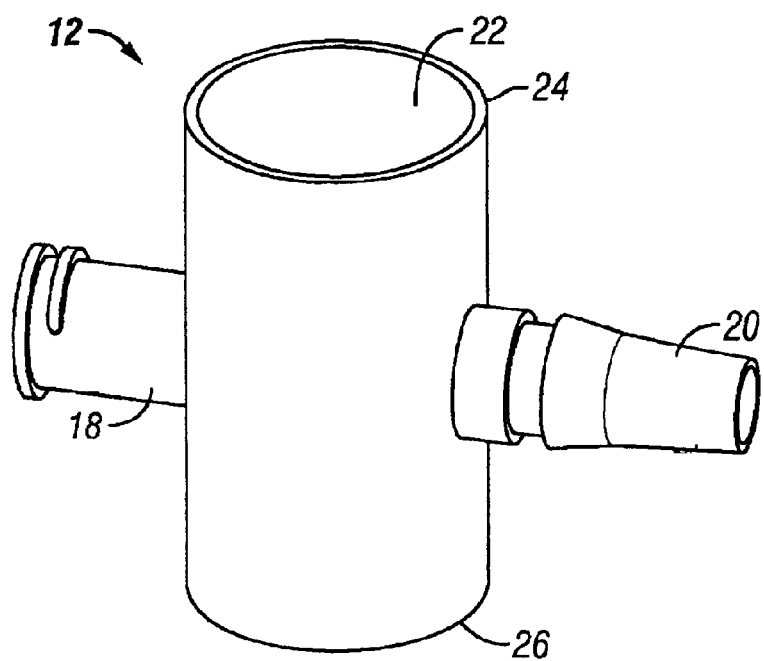
FIG. 3 is a perspective view of a stopcock housing of the present invention.

The housing 12 is best shown in FIG. 3 and includes at least one inlet port 18 and at least one outlet port 20. Both ports 18 and 20 lead into an interior cavity 22 sized to receive the valve member 14. Notably, the housing 12 is open at a first end 24 and a second end 26, defining the limits of the interior cavity 22. The importance of these open ends 24 and 26 is discussed below.

Figure 4:
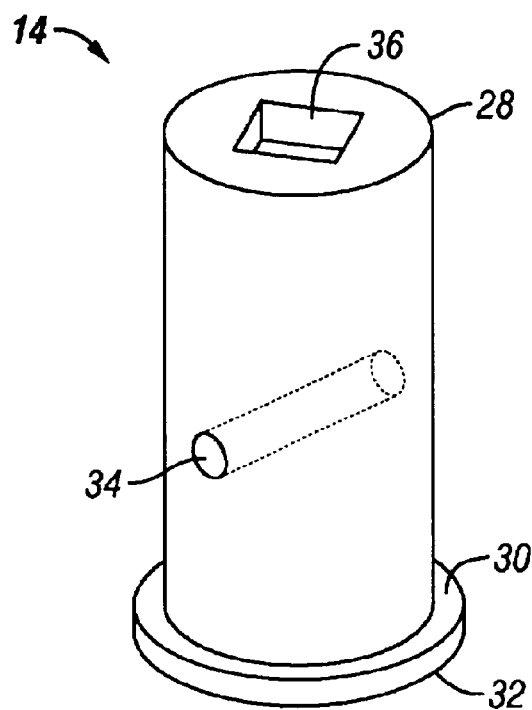
FIG. 4 is a perspective view of a valve member of the present invention.

FIG. 4 shows a valve member 14. The valve member 14 generally comprises a cylinder sized to be rotatably contained within the interior cavity 22. The valve member 14 includes a first end 28 and a second end 30 that correspond to the first and second ends 24 and 26 of the housing 12 when assembled. The second end 30 of the valve member 14 includes a stop 32 preferably in the form of a flange. The stop 32 is sized to interfere with the opening at the second end 26 of the housing 12. The stop 32 thus prevents the valve member 14 from being removed from the housing 12 through the first end 24 of the housing 12. The valve member 14 further includes a passage 34 that is alignable with the ports 18 and 20 of the housing 12 when it is desired to establish fluid communication between the ports 18 and 20. Additionally, at the first end 28 of the valve member 14, there is an attachment area 36, usable to attach the valve member 14 to the handle member 16.

The handle member 16 is shown in FIG. 2 and includes an attachment area 38 that is configured to mate with the attachment area 36 of the valve member 14. The attachment areas 36 and 38 are shown in FIGS. 2 and 4 as being square female and male couplings, respectively. One skilled in the art will understand that many configurations would perform the desired function of attaching the handle member 16 to the valve member 14. The male and female coupling arrangement shown in the Figures serves to provide adequate surface area for the application of adhesive, if desired, and also provides sufficient structural interaction between the valve member 14 and the handle member 16 to allow the handle member 16 to be used to twist the valve member 14. The handle member 16 further includes a contact surface 40. When the handle member 16 is attached to the valve member 14, the contact surface 40 acts against the first end 24 of the housing 12. The contact surface 40 and the stop 32 together prevent the valve member 14 from moving axially, relative to the housing 12. Thus the valve member 14 is axially locked within the housing 12, yet still allowed to rotate.

Figure 2A:
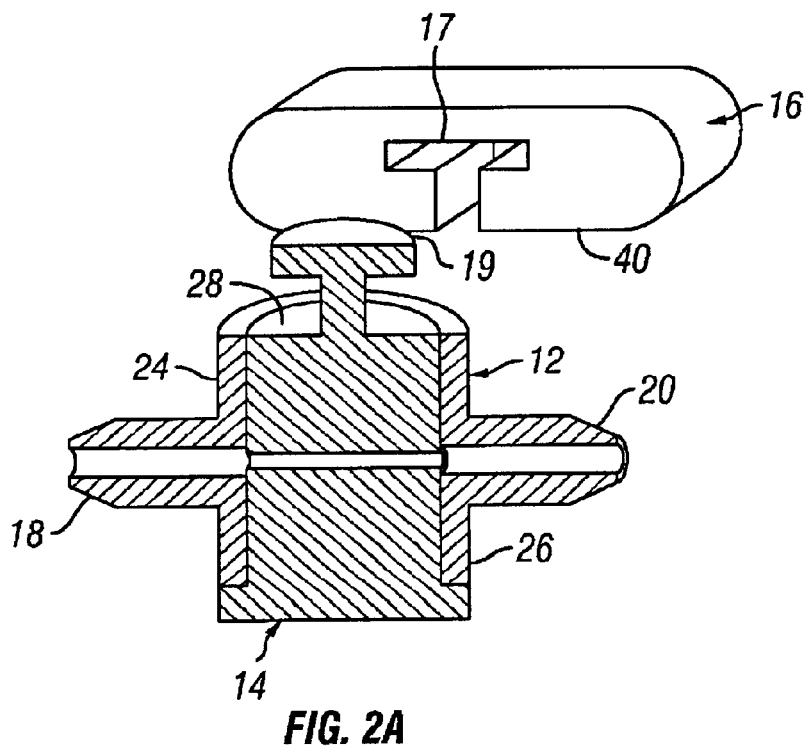
FIG. 2A is a perspective sectional view of an alternative embodiment of a stopcock of the present invention with the handle member separated from the valve member.

FIG. 2A shows an alternative preferred configuration for attaching the handle member 16 to the valve member 14. Handle member 16 includes a slot 17 configured to mate with a valve member extension 19. Preferably the valve member extension 19 forms a snap lock fit with the slot 17. When the handle member 16 is snapped onto the valve member 14, the underside of the handle member 16 forms the contact surface 40, which acts against the first end 24 of the housing 12 to prevent the valve member 14 from becoming disengaged from the housing 12.

The materials used to make the housing 12, the valve member 14, and the handle member 16, are preferably clear and gamma-stable, and thus allow the entire valve to be assembled and packaged prior to sterilization using gamma irradiation. Depending on the manufacturing method chosen to make the valve 10, discussed below, the materials used in the housing 12, the valve member 14, and the handle member 16 may be the same or different. For example, to reduce costs, the handle member may be made out of less expensive, non-gamma-stable materials. Acetal and ABS provide two examples of acceptable materials.

Gamma-stable materials, acceptable for use in making the valve 10 of the present invention include PEEK, polyesters, PETG, polycarbonate, polycarbonate alloys, polysulfone, polyurethane, PEKK, polyetherimide, thermosets, polyamides, PAEK, and flouroplastics other than PTFE and FEP. Examples of acceptable thermosets include polyimides, polyurethanes, and polyesters. These materials are provided by way of example and are not intended to represent an exclusive list of acceptable materials. Any gamma-stable material exhibiting sufficient structural integrity is acceptable.

Once materials are selected and used to form the housing 12, valve member 14 and handle member 16, the valve 10 is assembled by introducing the first end 28 of the valve member 14 into the second end 26 of the housing 12. The valve member 14 slides into the interior cavity 22 of the housing 12 until the stop 32 abuts against the second end 26 of the housing 12. Next the handle member 16 is attached to the valve member 14 by aligning the respective attachment areas 36 and 38 with each other, and securing them together using a gamma-stable adhesive, ultrasonic weld, mechanical connection, or the like.

Figure 5:
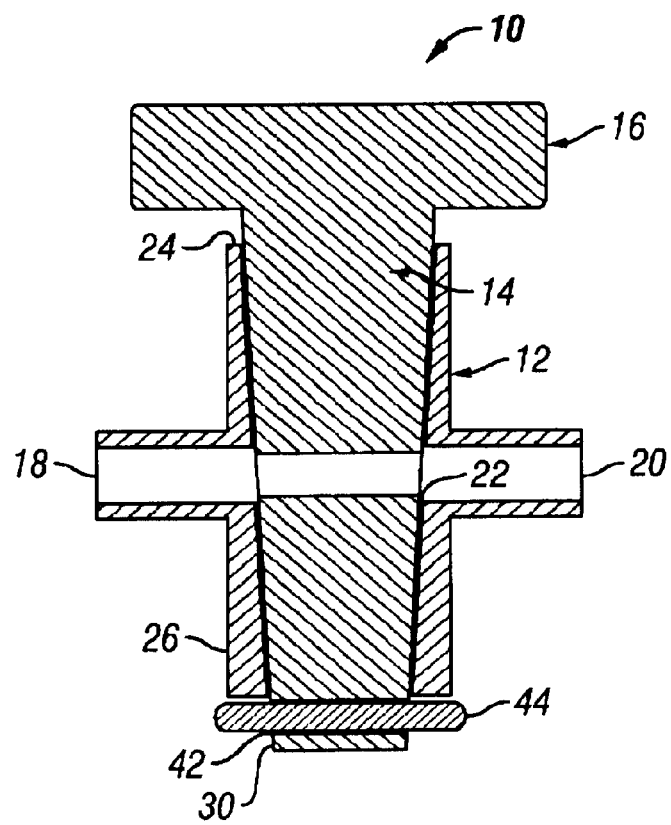
FIG. 5 is a cutaway elevation of another preferred embodiment of the stopcock of the present invention.

Various embodiments of the present invention provide a stopcock 10 whereby the handle member 16 and the valve member 14 are integral. One such embodiment is shown in FIG. 5. The valve member 14 defines a hole 42 at its second end 30 through which a pin 44 is placed after the valve member 14 is inserted into the housing 12. A stop (not shown) may be provided to act against the first end 24 of the housing 12, such as stop 40 shown in FIG. 2. Alternatively, as shown in FIG. 5, the valve member 14 and the interior cavity 22 are slightly conical, obviating the need for a stop 40, and better ensuring a seal is formed between the valve member 14 and the housing 12. The hole 42 is placed to create a slight downward force on the valve member 14 when the pin 44 is in place.

Figure 6:
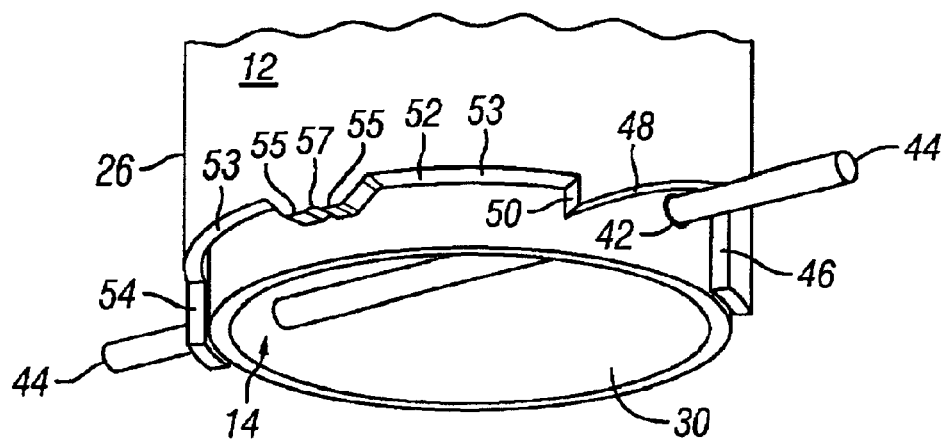
FIG. 6 is a partial perspective view of an embodiment of the second end of the housing of the present invention.

FIG. 6 shows an embodiment of a housing 12 that is shaped to increase the downward force on the valve member 14. The second end 26 of the housing 12 is shaped to form a recessed area 46 that provides adequate clearance to place the pin 44 through the hole 42 in the valve member 14, when the hole 42 is aligned with the recessed area 46.

Adjacent to the recessed area 46 is an angled ramp surface 48. Once the pin 44 is in place, the valve member 14 is rotated so that the pin 44 meets with increasing resistance by the ramp surface 48, as the valve member 14 is pulled deeper into the interior cavity 22. If the valve member 14 and interior cavity 22 are conical, this ramp effect creates a greater seal between the side wall of the valve member 14 and the inner side wall of the housing 12 defining the interior cavity 22. If a cylindrical valve member 14 and interior cavity 22 are used, along with a stop 40 such as that shown in FIG. 2, the ramp effect creates a tighter seal between the stop 40 and the first end 24 of the housing 12.

At the end of the angled ramp surface 48 is a catch 50. Once the valve member 14 is rotated sufficiently, the pin 44 will overcome the ramp 48 and snap behind the catch 50. The catch 50 prevents counter rotation of the valve member 14 to the extent that the pin 44 reenters the recessed area 46 and becomes dislodged. The catch 50 thus defines a rotational limit on the valve member 14.

Adjacent the catch 50 is an operating surface 52. This surface 52 is relatively parallel to the plane the pin 44 defines as the valve member 14 is rotated. Preferably, the operating surface 52 also includes level portions 53 and tightening portions 55. The level portions 53 are positioned to provide a minimal amount of downward force on the pin 44 so the valve member 14 may be rotated with ease. The tightening portions 55 are positioned to correspond with alignment positions between the valve member passage 34 and the housing ports 18 and 20. Thus, when the valve member 14 is in alignment with the ports of the housing 12, the valve member 14 is pulled into tight contact with the interior walls of the housing 12, thereby creating a fluid-tight seal acceptable for high pressure operation. A notch 57 may be included to provide a tactile feedback to the operator as to when the valve member 14 is in alignment with the housing ports 18 and 20. The angular operating range of the valve member 14 is defined at one extreme by the catch 50, as discussed above, and is defined at an opposite extreme by a rotational stop 54. The rotational stop 54 prevents the pin 44 from rotating to the point where it enters the recessed area 46 on the opposite side of the housing 12, designed to accommodate the other end of the pin 44.

Figure 7:
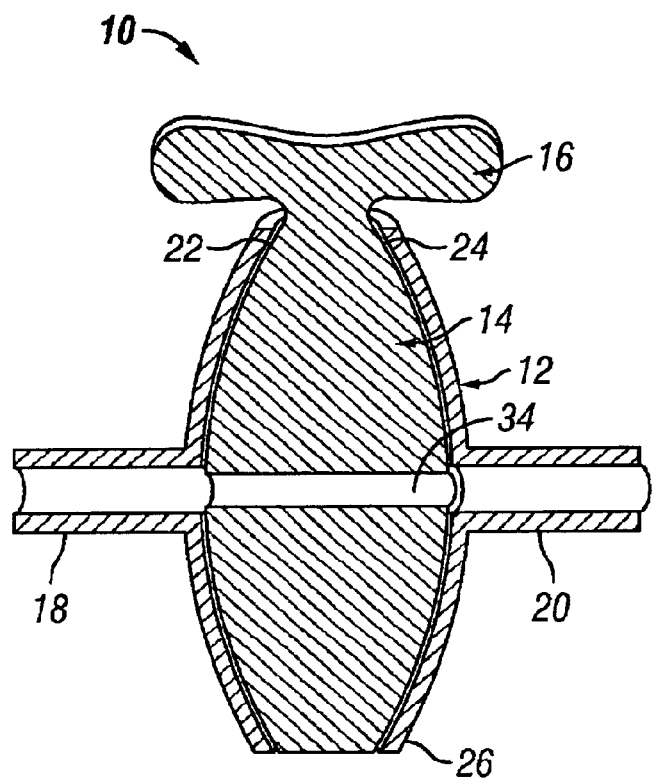
FIG. 7 is a cutaway elevation of yet another preferred embodiment of the stopcock of the present invention.

One manufacturing method of the present invention allows the use of a valve member 14, which is integral with a handle member 12, and does not require the use of a pin 44. FIG. 7 shows an embodiment of stopcock 10 whereby the valve member 14 and the interior cavity 22 of the housing 12 are curved such that the first end 24 and the second end 26 of the housing 12 are narrower than the other parts of the housing 12. Thus, the valve member 14 is locked inside the housing 12.

To manufacture the stopcock 10 of FIG. 7, the valve member 14 is molded of a first gamma-stable material. A rod (not shown) is then placed through the passage 34 to keep the passage 34 open during the remainder of the manufacturing process and to form the inlet port 18 and outlet port 20 of the housing 12. The housing 12 is then cast around the valve member 14 and rod using a second gamma-stable material that has a lower melting temperature than that of the first gamma-stable material. Using materials with different melting points and different molding temperatures ensures that the valve member 14 won't melt and adhere to the housing 12. A light agent, such as a lubricant, may be applied to the valve member 14 to further prevent the housing 12 from adhering thereto. For example, PEEK may be used as a first material to make the valve body 14. Polycarbonate could then be used as the second material to mold the housing 12. Polycarbonate has a melting temperature of about 540–575° F. but a relatively low molding temperature of about 150–220° F.

Once the housing 12 has solidified, the rod is removed and the valve member 14 may be rotated within the housing 12. An alternative to casting the housing 12 around the valve member 14 is a dip coating process whereby the valve member 14 and rod are repeatedly dipped into a liquid volume of the second material to form the housing 12.

Figure 8:
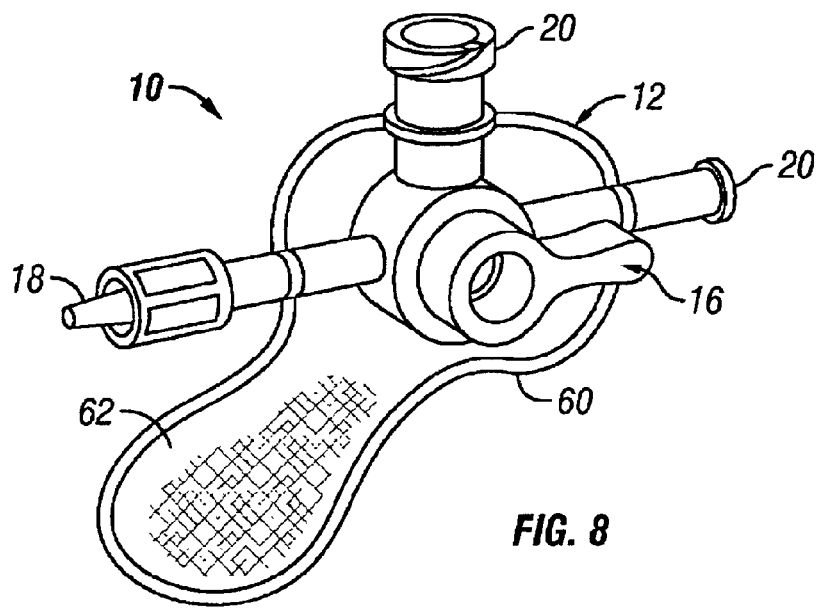
FIG. 8 is a perspective view of a preferred embodiment of a stopcock of the present invention.

FIG. 8 is a preferred embodiment of the stopcock 10 of the present invention. The stopcock 10 is shown as a three-way stopcock with one inlet port 18 and two outlet ports 20. A flange 60 is integral with the ports 18 and 20 and extends therefrom. The flange 60 may be a different material than the rest of the housing 12 but is preferably the same material. The flange 60 adds rigidity to the housing 12 for high pressure operations and also provides an area 62 to grip the valve 10 while turning the handle member 16. Gripping the flange 60 provides increasing turning power and prevents fingers from interfering with the movement of the handle member 16.

Figure 9:
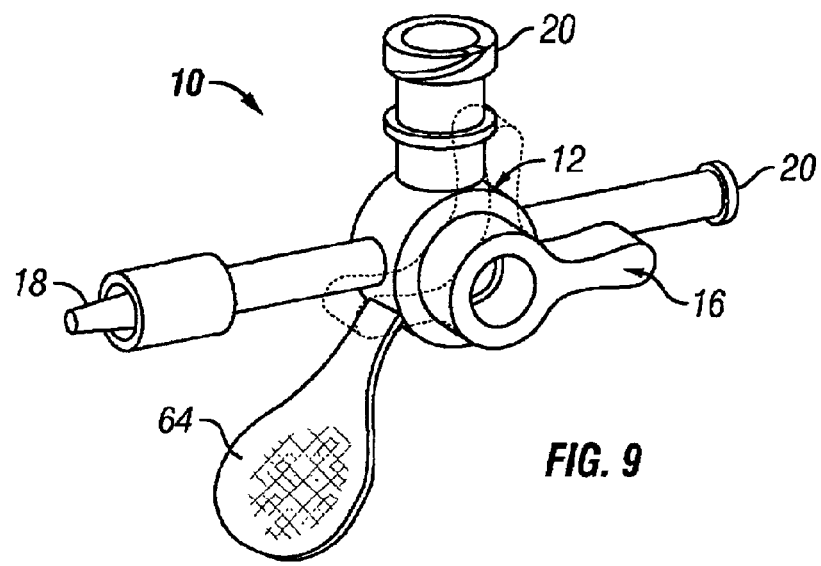
FIG. 9 is a perspective view of another preferred embodiment of a stopcock of the present invention.

FIG. 9 is another preferred embodiment of the stopcock 10 of the present invention. The stopcock 10 is shown as a three-way stopcock with one inlet port 18 and two outlet ports 20. A grip 64 extends from the housing 12 at an angle that does not interfere with the range of motion of the handle member 16, the various positions of which are shown in phantom lines. Like the flange 60 shown in FIG. 8, using the grip 64 increases turning power and prevents fingers from interfering with the movement of the handle member 16.

The foregoing description addresses embodiments encompassing the principles of the present invention. The embodiments may be changed, modified and/or implemented using various types of arrangements. For example, the stopcock of the present invention has been herein described as pertaining to medical applications. However, it is envisioned, and would be clear to one skilled in the art, that the teachings of the present invention could be applied to applications in fields such as electronics, microbiology, or others requiring sterility. Thus, those skilled in the art will readily recognize various modifications and changes that may be made to the invention without strictly following the exemplary embodiments and applications illustrated and described herein, and without departing from the scope of the invention, which is set forth in the following claims.

What is claimed is:

1. A stopcock, capable of withstanding gamma irradiation, comprising:
    a housing constructed from gamma-stable material defining an inlet port, at least one outlet port, and an interior cavity having an inner diameter and open at two opposing ends;
    a valve member constructed from gamma-stable material rotatably contained within said interior cavity, defining a passage alignable with said ports, and having:
        an outer diameter substantially equal to said inner diameter; and,
        a stop at an end of said valve member extending radially therefrom such that said stop is unable to pass through said cavity; and,
    a handle member, attached to an opposite end of said valve member, constructed and arranged to allow rotation of said valve member and to prevent said valve member from becoming separated from said housing.

2. The stopcock of claim 1 further comprising a weld connecting said handle member to said valve member.

3. The stopcock of claim 1 further comprising a pin connecting said handle member to said valve member.

4. The stopcock of claim 2 wherein said weld comprises an ultrasonic weld.

5. The stopcock of claim 1 further comprising an adhesive connecting said handle member to said valve member.

6. The stopcock of claim 1 wherein said housing comprises a material selected from the group: polyesters, PETG, polycarbonate, polycarbonate alloys, polysulfone, polyurethane, PEKK, PEEK, PAEK, polyetherimide, thermosets, polyamides, and flouroplastics other than PTFE and FEP.

7. The stopcock of claim 6 wherein said thermosets comprise the group: polyimides, polyurethanes, and polyesters.

8. The stopcock of claim 1 wherein said handle member comprises a material selected from the group: acetal and ABS.

9. The stopcock of claim 1 wherein said valve member comprises a material selected from the group: polyesters, PETG, polycarbonate, polycarbonate alloys, polysulfone, polyurethane, PEKK, PEEK, PAEK, polyetherimide, thermosets, polyamides, flouroplastics other than PTFE and FEP.

10. The stopcock of claim 9 wherein said thermosets comprise the group: polyimides, polyurethanes, and polyesters.

11. The stopcock of claim 1 wherein said handle member comprises a material selected from the group: polyesters, PETG, polycarbonate, polycarbonate alloys, polysulfone, polyurethane, PEKK, PEEK, PAEK, polyetherimide, thermosets, polyamides, flouroplastics other than PTFE and FEP.

12. The stopcock of claim 11 wherein said thermosets comprise the group: polyimides, polyurethanes, and polyesters.

13. The stopcock of claim 1 wherein said handle member and said valve member are made of the same material.

14. The stopcock of claim 1 wherein said valve member and said housing are made of the same material.

15. The stopcock of claim 1 wherein said valve member, said housing, and said handle member are all made of the same material.

16. The stopcock of claim 1 further comprising a flange, extending from the housing, providing a gripping area.

17. The stopcock of claim 16 wherein said flange is integral with the housing.

18. The stopcock of claim 1 wherein the at least one outlet port comprises one outlet port.

19. The stopcock of claim 1 wherein the at least one outlet port comprises two outlet ports.

20. A method of making a stopcock of claim 1, comprising:
    placing a valve member inside a valve housing;
    connecting a handle to the valve member, thereby locking the valve member inside the valve housing.

21. The method of claim 20 wherein connecting the handle to the valve member comprises ultrasonically welding the handle to the valve member.

22. The method of claim 20 wherein connecting the handle to the valve member comprises adhering the handle to the valve member.

23. A method of making a stopcock comprising:
    providing a valve member of a gamma-stable material, said valve member defining a passage therethrough;
    passing a pin through said passage;
    over molding a gamma-stable material around said valve member with said pin to form a housing around said valve member;
    preventing said housing from fusing with said valve member;
    removing said pin once said housing has solidified.

24. The method of claim 23 wherein said step of preventing said housing from fusing with said valve member comprises selecting a gamma-stable material having a melting temperature lower than that of said valve member for said step of over molding said valve member.

25. The method of claim 23 wherein said step of preventing said housing from fusing with said valve member comprises coating said valve member with a lubricant prior to performing said step of over molding said valve member.

26. A stopcock of claim 1, wherein:
    the handle member is usable to rotate said valve member around a predetermined range of motion; and further comprising:
        a grip, extending from said housing at a position selected so that a user's hand gripping said grip, will not interfere with rotation of said handle member around said predetermined range of motion.

27. The stopcock of claim 26 wherein said grip comprises a flange extending from said housing.

28. A stopcock comprising:
    a housing constructed from gamma-stable material and defining an inlet port, at least one outlet port, and an interior cavity having an inner diameter and open at two opposing ends;

a valve member constructed from gamma-stable material, said valve member rotatably contained within said cavity and defining a passage alignable with said ports;

a mechanism operably attached to an end of said valve member, constructed and arranged to prevent said valve member from passing completely through the interior cavity of said housing, and;

a handle member, operably attached to an opposite end of said valve member, constructed and arranged to allow rotation of said valve member and to prevent said valve member from becoming separated from said housing.

29. The stopcock of claim 28 wherein the at least one outlet port comprises one outlet port.

30. The stopcock of claim 28 wherein the at least one outlet port comprises two outlet ports.

31. The stopcock of claim 28 wherein said mechanism comprises a frustoconical inner side wall of said housing, defining said interior cavity, and a frustoconical section of said valve member, angled to mate with said housing inner side wall.

32. The stopcock of claim 28 wherein said mechanism comprises a stop at an end of said valve member extending radially therefrom.

33. The stopcock of claim 28 wherein said handle member comprises a pin extending through said valve member and sized to provide opposing pin ends extending radially beyond said housing for use by an operator to turn said valve member.

34. The stopcock of claim 28 wherein said housing and said valve member both comprise a material selected from the group: polyesters, PETG, polycarbonate, polycarbonate alloys, polysulfone, polyurethane, PEKK, PEEK, PAEK, polyetherimide, thermosets, polyamides, flouroplastics other than PTFE and FEP.

35. A stopcock comprising:

a valve member of a first gamma-stable material having a longitudinal axis and a passage therethrough transverse to said longitudinal axis;

a housing of a second gamma-stable material formed around the valve member, the housing having at least one open end and defining at least one inlet port and at least one outlet port, the ports alignable with the passage;

whereby the valve member has varying circular cross-sectional areas measured in planes perpendicular to the longitudinal axis, cross-sectional areas toward a middle of the valve member being greater than the cross-sectional areas toward ends of the valve member, and the housing defines an inner cavity sized to closely complement the valve member;

and whereby the valve member and housing are shaped to allow rotation of the valve member around the longitudinal axis, relative to the housing, and to prevent movement in either direction along the longitudinal axis, relative to the housing.

36. The stopcock of claim 35 wherein said first and second materials are different materials.

37. The stopcock of claim 35 wherein said housing further comprises a closed end, wherein the open end defines an opening having a cross-sectional area smaller than the cross-sectional areas toward the middle of the valve member.

* * * * *